United States Patent [19]

Stoy et al.

[11] Patent Number: 4,919,130
[45] Date of Patent: Apr. 24, 1990

[54] TOOL FOR INSERTING COMPRESSIBLE INTRAOCULAR LENSES INTO THE EYE AND METHOD

[75] Inventors: Michael A. Stoy, Redmond; Vaclav Dusek, Renton; Anilbhai S. Patel, Seattle, all of Wash.; Ray G. Herriott, Grand Island, Nebr.

[73] Assignee: Nestle S.A., Switzerland

[21] Appl. No.: 115,231

[22] Filed: Nov. 2, 1987

Related U.S. Application Data

[63] Continuation-in-part of Ser. No. 928,057, Nov. 7, 1986, abandoned.

[51] Int. Cl.$^5$ .............................................. A61B 17/00
[52] U.S. Cl. .................................................. 606/107
[58] Field of Search ...................... 128/303 R; 623/6

[56] References Cited

U.S. PATENT DOCUMENTS

| | | |
|---|---|---|
| 3,991,426 | 11/1976 | Flom et al. . |
| 4,053,953 | 10/1977 | Flom et al. . |
| 4,136,406 | 1/1979 | Norris . |
| 4,198,980 | 4/1980 | Clark . |
| 4,214,585 | 7/1980 | Bailey, Jr. . |
| 4,251,887 | 2/1981 | Anis . |
| 4,326,306 | 4/1982 | Poler . |
| 4,373,218 | 2/1983 | Schachar . |
| 4,423,809 | 1/1984 | Mazzocco . |
| 4,573,998 | 3/1986 | Mazzocco . |
| 4,585,457 | 4/1986 | Kalb . |
| 4,600,003 | 7/1986 | Lopez . |
| 4,615,703 | 10/1986 | Callahan et al. ........... 128/303 R X |
| 4,681,102 | 7/1987 | Bartell .............................. 128/303 R |
| 4,747,404 | 5/1988 | Jampel et al. . |

FOREIGN PATENT DOCUMENTS

| | | |
|---|---|---|
| 2467589 | 4/1987 | France . |
| 2114315A | 8/1983 | United Kingdom . |
| 2180759A | 9/1985 | United Kingdom . |

*Primary Examiner*—Michael H. Thaler
*Attorney, Agent, or Firm*—Paul E. Krieger; Sally Yeager

[57] ABSTRACT

The tool and method for preparing for insertion into an eye an intraocular lens formed of a compressible material includes an elongated hollow chamber with an inlet end and an outlet end. An intraocular lens formed of a compressible material is extruded to a smaller size that fits in the elongated chamber by a compresser which includes an outlet adapted to be aligned with the inlet end of the elongated chamber. The extruded intraocular lens is pushed through the elongated chamber from the inlet end through to the outlet end.

48 Claims, 12 Drawing Sheets

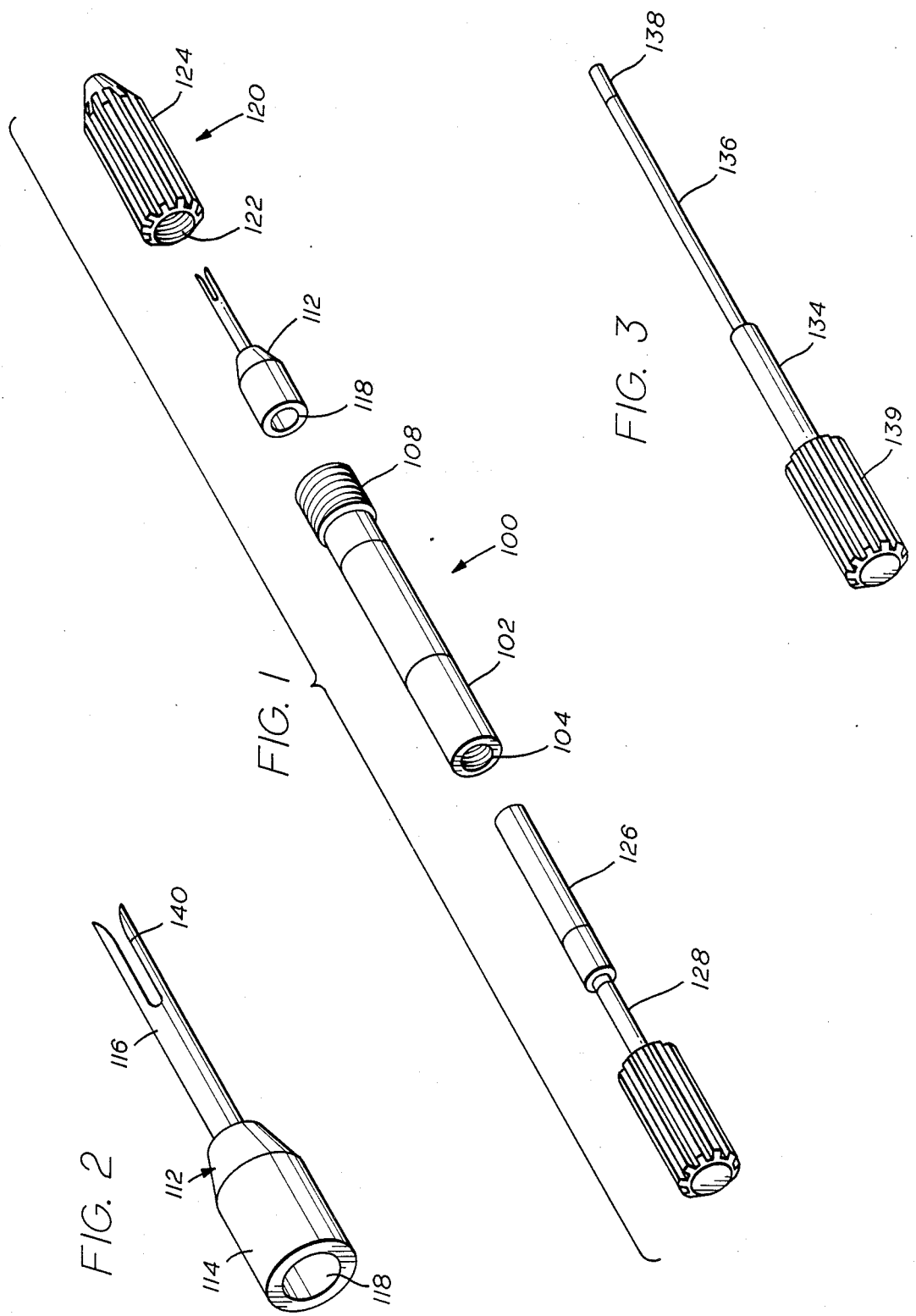

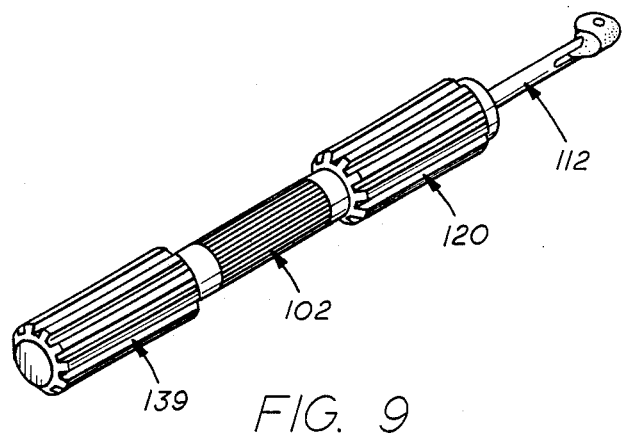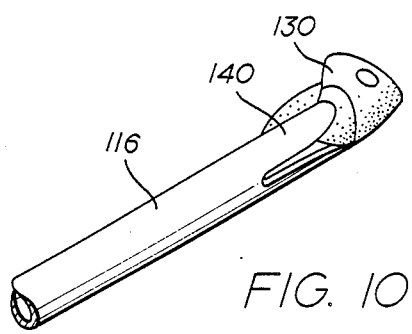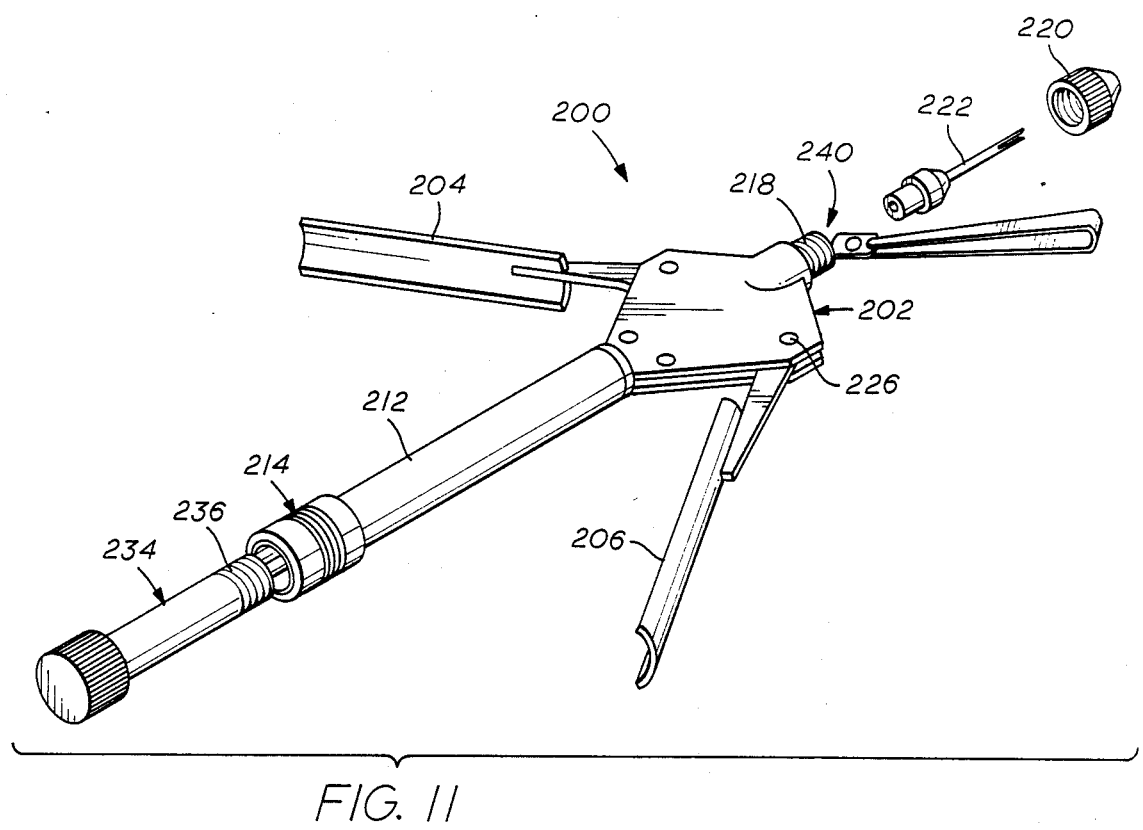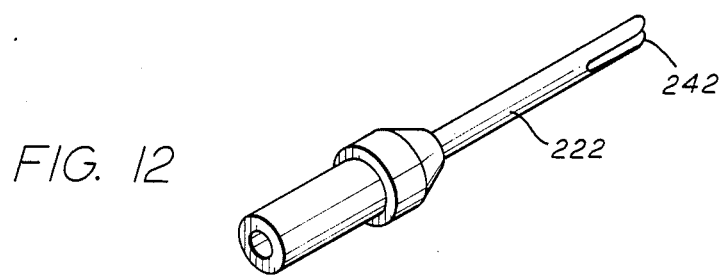

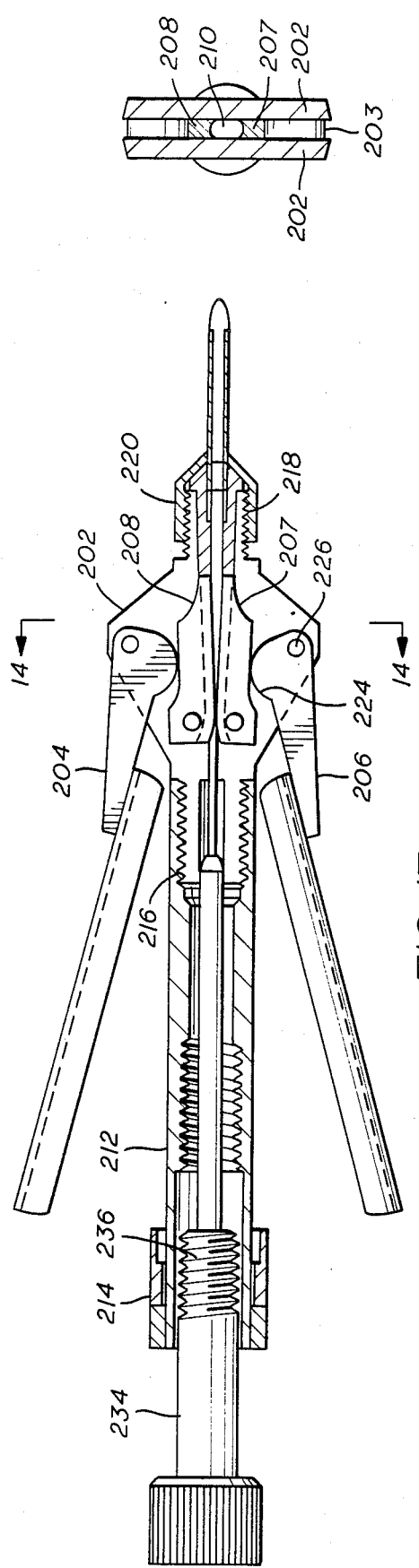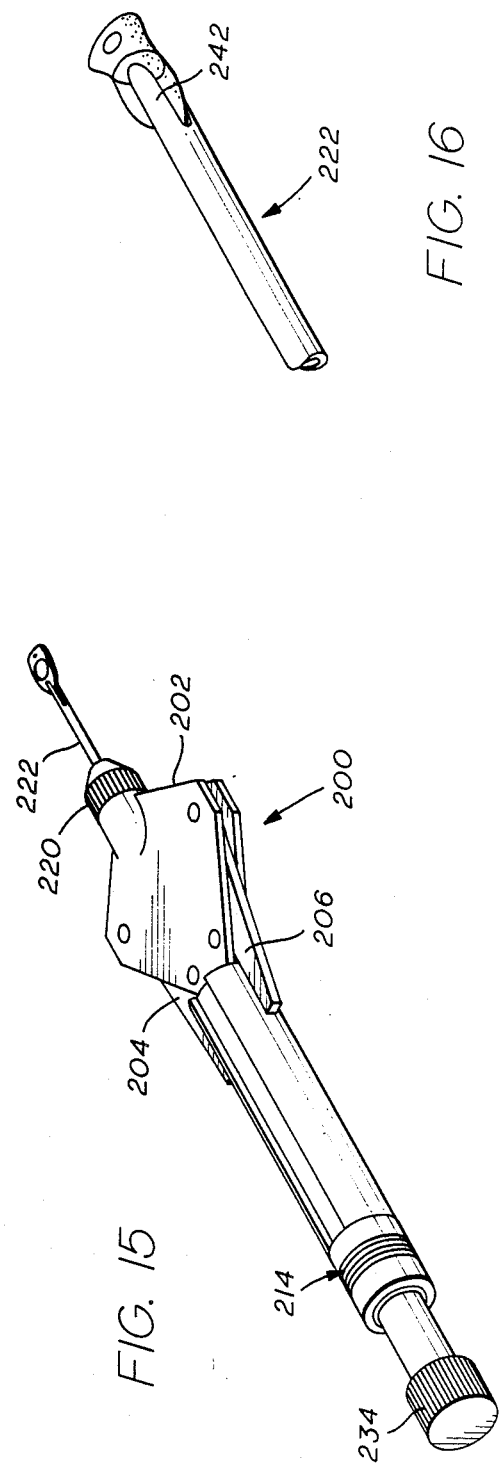
FIG. 14
FIG. 16
FIG. 13
FIG. 15

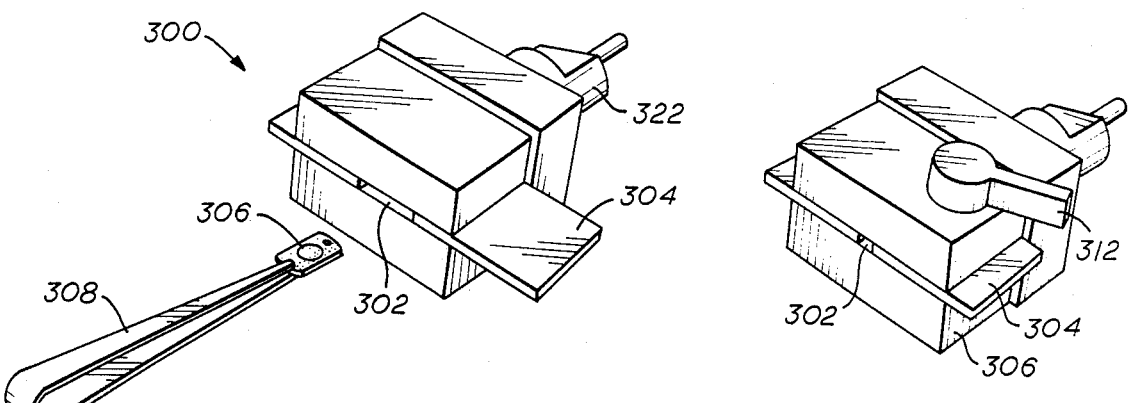
FIG. 20
FIG. 21
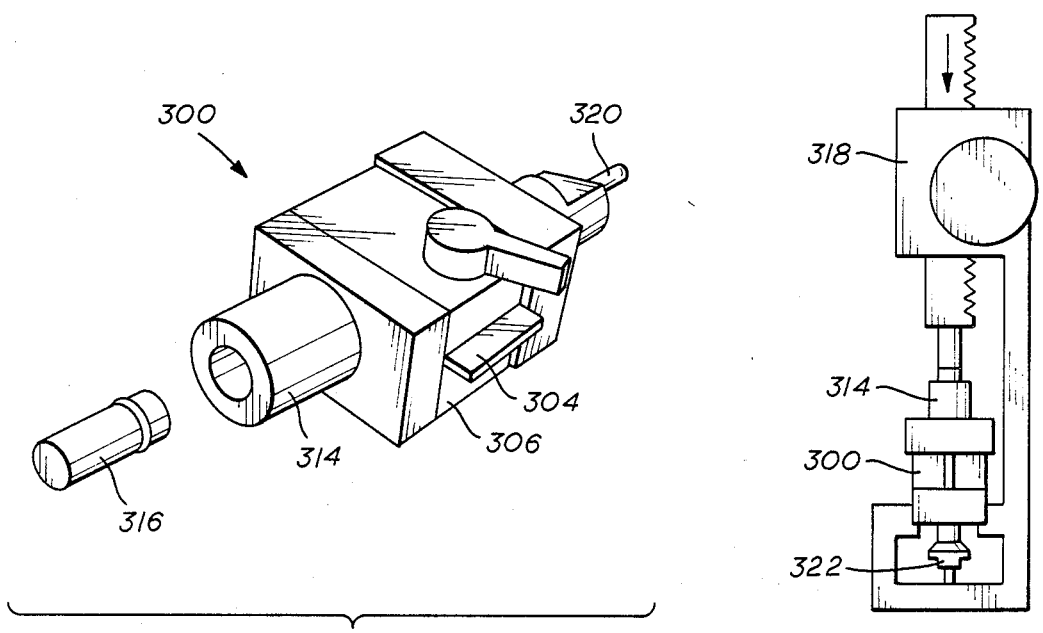
FIG. 22
FIG. 23

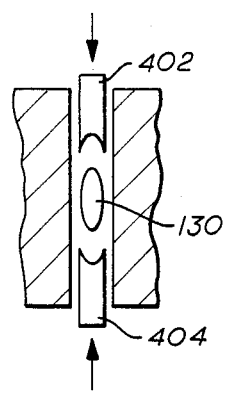
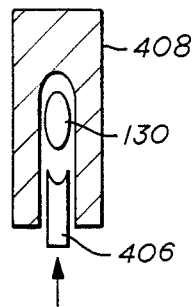
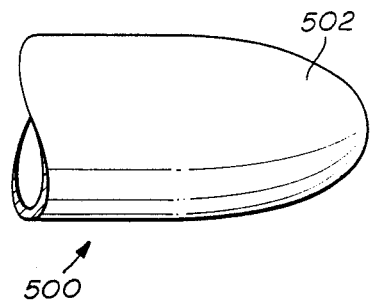
FIG. 28　　　FIG. 29　　　FIG. 30
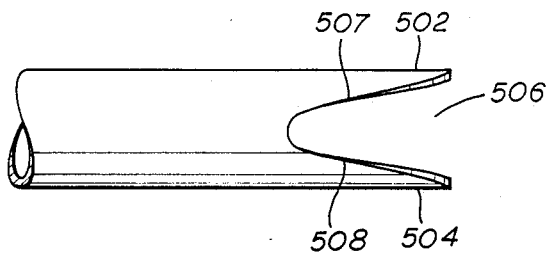
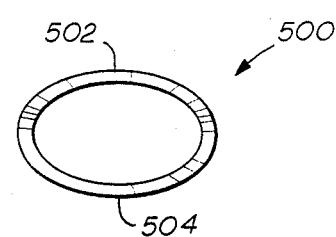
FIG. 31　　　　　　　　FIG. 32
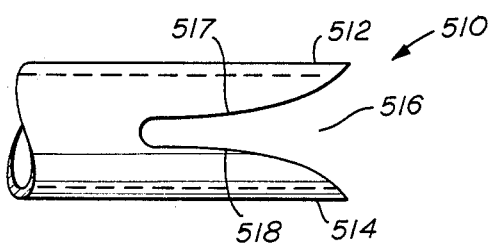
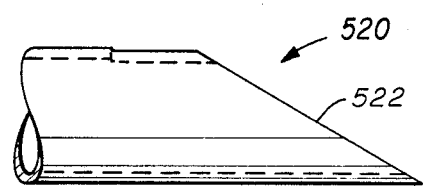
FIG. 33　　　　　　　　FIG. 35
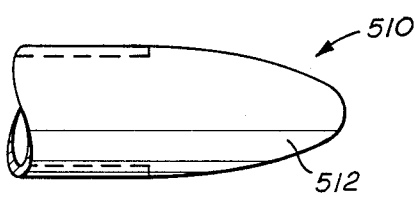
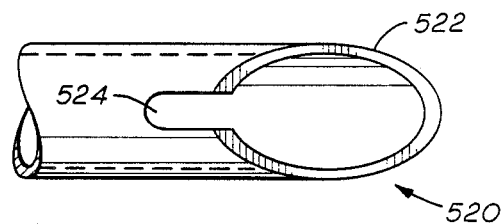
FIG. 34　　　　　　　　FIG. 36
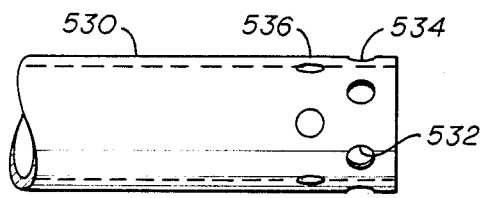
FIG. 37

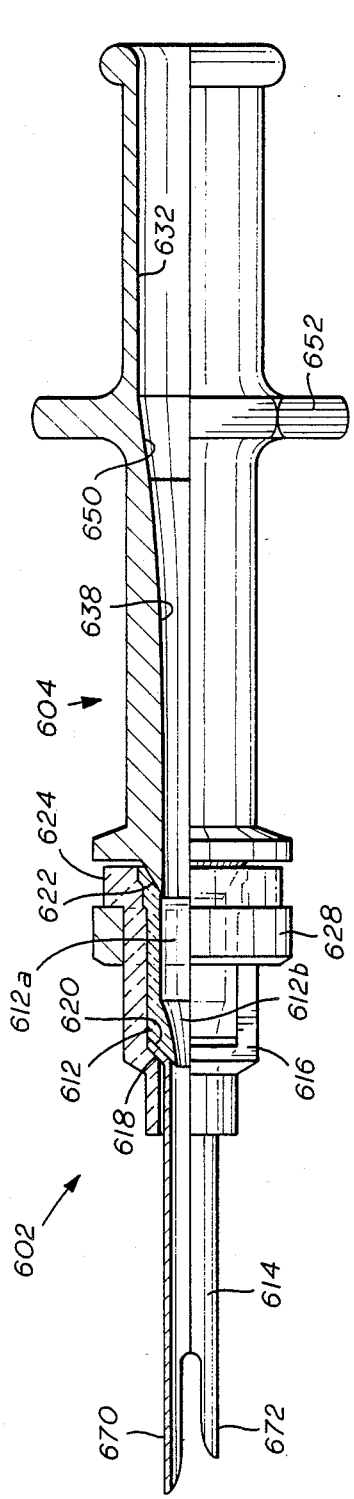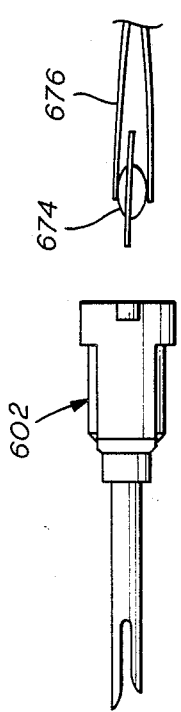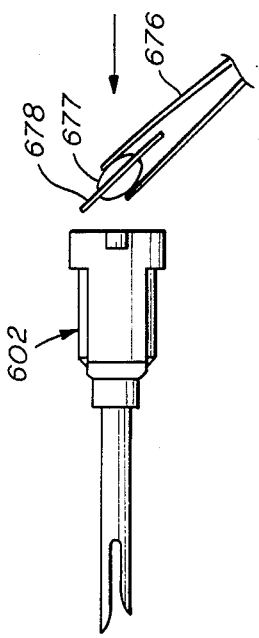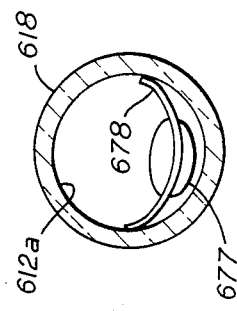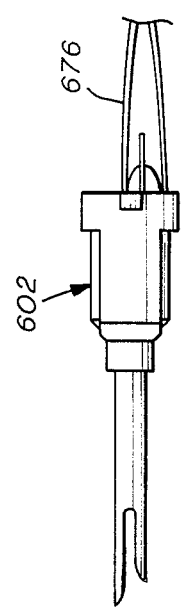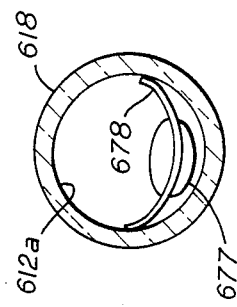

TOOL FOR INSERTING COMPRESSIBLE INTRAOCULAR LENSES INTO THE EYE AND METHOD

BACKGROUND OF THE INVENTION

This is a continuation-in-part of application Ser. No. 928,057 filed on November 7, 1986, abandoned, whose entire contents are hereby incorporated by reference.

The present invention relates to tools and methods for inserting compressible intraocular lenses into the eye, and more particularly into the eye through as small an incision as possible including that for phacoemulsification methods of cataract surgery.

Numerous procedures for the removal of cataracts have been developed in which the natural lens is removed from the eye and replaced by an artificial lens implant, a so-called intraocular lens. While implantation of intraocular lenses is considered to be a relatively safe procedure, one of the principal disadvantages of conventional rigid intraocular lenses is that implantation of the lens requires a relatively large incision in the ocular tissue, which could result in complications such as an increased risk of post-operative astigmatism, prolonged healing period, laceration of the ocular tissues particularly with respect to the cornea and the pupil.

Lenses have recently been developed which are deformable and thus able to fit through relatively small incisions in the ocular tissue into the internal chambers of the eye. Small incision insertion surgery decreases the post-operative healing and rehabilitation time as well as the potential complication of suturing induced astigmatism.

These lenses are designed to retain a prescribed configuration once implanted in the central optical area and have prescribed memory characteristics which enable the lens to be deformed to fit through a smaller ocular incision and then reformed once in the eye. The construction and design of some of these lenses and known methods for implanting them are described in U.S. Pat. No. 4,573,998 to Mazzocco, the contents of which are hereby incorporated by reference in their entirety.

One example of a device for inserting a deformable lens is the Faulkner Folder TM for Staar silicone lenses. Faulkner holding forceps are used to hold the silicone lenses which are then folded by the inserting device. The Staar insertion device, however, merely folds the lens without compressing it and thus does not really reduce the cross-sectional area of the lens. As such, the size of the incision required for insertion is not necessarily or significantly reduced for most lenses required for implantations which are greater than 18 diopters. The refractive index of the material of the intraocular lens, the dioptric power of the intraocular lens, the thickness and width of the intraocular lens are factors which ultimately decide the cross-sectional area of the unfolded and subsequently folded lens which in turn may require an insertion channel for this approach that is much larger than acceptable.

Also, folding of a lens as this approach requires may not always be possible for high diopter, thicker lenses of certain materials. Further, this approach not only requires a larger incision, but it also does not permit release of the lens in a controlled manner due to the stored elastic energy from the bending. This could possibly result in damage to the cornea or other portions of the eye if the lens should spring loose from the lens holder.

OBJECTS OF THE INVENTION

Accordingly, it is the principal object of the present invention to provide an improved method and instrument for inserting compressible intraocular lenses through small incisions in the eye.

Another object of the present invention is to provide a novel tool for inserting a compressible intraocular lens into the eye which results in a reduced size of the opening required for insertion.

A further object of the present invention is to provide an improved insertion tool which reduces the cross-sectional area of the lens by extruding it and thereby allows insertion through a smaller opening.

A still further object of the present invention is to provide an improved insertion instrument which prevents the lens from becoming misaligned or from snagging the edge of the incision during insertion thereof into the eye.

Another object is to provide an improved insertion tool which prevents the compressible lens from damaging the cornea or other tissue of the eye upon release in the eye.

A further object is to provide a unique method of reducing the cross-sectional area of the optical zone of a compressible intraocular lens so it can be inserted into and delivered through a small cannula system into the eye.

A further object is to provide a novel loading system which eliminates the need to hand roll the intraocular lens into an insertion tool.

Another object is to provide an improved instrument and method which increase the speed and accuracy of the process for loading a compressible intraocular lens into the eye.

A further object is to provide an improved insertion tool which delivers the intraocular lens into the eye in a more controlled manner.

A still further object is to provide a novel insertion tool which minimizes the need to physically handle the lens after it has been lubricated.

Another object is to provide an improved insertion tool design which decreases the likelihood of the insertion tool contacting or touching the corneal endothelium or other ocular structures when releasing the lens in the eye.

A further object is to provide an improved insertion tool which can load compressible lenses having larger cross-sectional areas into an insertion tubing.

A still further object is to provide an improved system for inserting foldable intraocular lenses into the eye without damaging the lens, with minimal resulting trauma to the eye, and which minimizes the amount of manual manipulation of the lens required.

Another object is to provide a novel apparatus and method for controllably inserting an elastomeric intraocular lens of about six mm optic diameter through an ocular incision of approximately the size required for a standard phacoemulsification tip, which is about 3.0 to 3.5 mm or with minimum enlargement of this incision depending upon the material and the diopter power of that intraocular lens.

A further object is to provide an intraocular lens insertion tool whose tip inserts easily into the eye and is configured to minimize the likelihood of damage to the capsular bag during the insertion procedure.

A still further object is to provide an improved intraocular lens insertion tool which is easy to load and to operate.

Another object is to provide a novel intraocular lens insertion tool that is easily and inexpensively manufactured such as to be disposable after a single use.

Other objects and advantages of the present invention will become more apparent to those persons having ordinary skill in the art to which the present invention pertains from the following description taken in conjunction with the accompanying drawings.

BRIEF DESCRIPTION OF THE DRAWINGS

FIG. 1 is a perspective view of an insertion tool of the present invention wherein the parts thereof are illustrated in exploded relation.

FIG. 2 is an enlarged view taken about line 2—2 of FIG. 1.

FIG. 3 is a perspective view of a push rod to be used with the tool of FIG. 1.

FIG. 9 is a perspective view of the insertion tool of FIG. 1 showing the lens being ejected from the cannula tip.

FIG. 10 is an enlarged view of the cannula tip taken about line 10—10 of FIG. 9 illustrating an extruded lens being ejected.

FIG. 11 is a perspective view of a tool illustrating another embodiment of the present invention with the parts shown in exploded relation.

FIG. 12 is an enlarged perspective view taken on line 12—12 of FIG. 11.

FIG. 13 is a side cross-sectional view of the insertion tool of FIG. 11.

FIG. 14 is a cross-sectional view taken about line 14—14 of FIG. 13.

FIG. 15 is a perspective view of the insertion tool of FIG. 11 illustrated in its ready to insert condition.

FIG. 16 is an enlarged view taken on line 16—16 of FIG. 15 illustrating a squeezed lens being ejected.

FIGS. 17 through 24 illustrate in simplified form an insertion tool system illustrating another embodiment of the present invention.

FIG. 17 is a perspective view of the loading block of this embodiment illustrated in isolation.

FIG. 18 is a front elevational view of the loading block of FIG. 17 illustrating the movement of the sliding plate thereof.

FIG. 19 illustrates the cannula alignment procedure thereof.

FIG. 20 illustrates the preloading of the intraocular lens step.

FIG. 21 illustrates the intraocular lens compression step.

FIG. 22 illustrates the loading of the cannula step.

FIG. 23 is a top plan view of FIG. 22 illustrating the transfer of the intraocular lens into the cannula step.

FIG. 24 illustrates the removal of the cannula with the lens in it from the loading block step.

FIG. 28 is an end elevational view of the assembly of FIG. 27.

FIG. 29 is a view similar to FIG. 28 illustrating a single slide variant.

FIG. 30 is a plan view of a first embodiment of a tip of the cannula of any of the insertion tools of the present invention.

FIG. 31 is a side view of the cannula tip of FIG. 30.

FIG. 32 is a front view of the cannula tip of FIGS. 30 and 31.

FIG. 33 is a side view of a second embodiment of a cannula tip of the present invention.

FIG. 34 is a plan view of the cannula tip of FIG. 33.

FIG. 35 is a side view of a third embodiment of a cannula tip of the present invention.

FIG. 36 is a plan view of the cannula tip of FIG. 35.

FIG. 37 is a plan (or elevational) view of a fourth embodiment of a cannula tip of the present invention.

FIG. 47 is a side view partially in section of the assembled cannula body and plunger housing of FIG. 42.

FIG. 48 illustrates a first step of the procedure for loading the lens into the loading chamber of the tool of FIG. 42.

FIG. 49 illustrates a second step of the loading procedure.

FIG. 50 illustrates a third step of the loading procedure.

FIG. 51 illustrates a fourth step of the loading procedure.

FIG. 52 is an end elevational view of the loading chamber showing the lens loaded therein after completion of the fourth step as shown in FIG. 52.

DETAILED DESCRIPTION OF THE PREFERRED EMBODIMENTS

Figure 4:
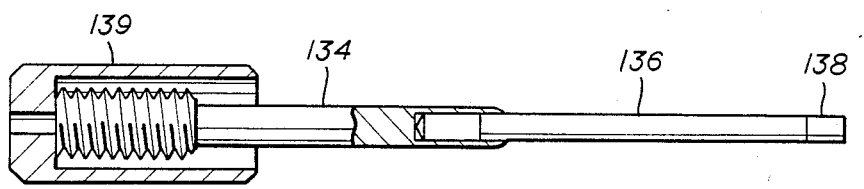
FIG. 4 is a side cross-sectional view of the push rod of FIG. 3.

Referring to FIg. 1 an insertion tool of the present invention is illustrated generally at 100. Tool 100 includes a tubular body 102 having a smooth inner surface and an internal thread 104 at its proximal or tail end and a threaded or male coupling 108 at its opposite distal or head end. The tubular body functions as a plunger housing.

A cannula is provided as shown at 112 in FIG. 1, and in isolation and greater detail in FIG. 2. The cannula 112 includes a cannula head 114 and an attached cannula member 116 in the form of a cylindrical, elliptical, oval or diamond shaped tube. The cannula head 114 comprises a compressing chamber and defines an inner loading chamber 118 and loading inlet which includes a cylindrical passageway section 118a and a tapered or conical passageway section 118b that converges towards and protrudes into the cannula member 116 and comprises a compressing portion of the compressing chamber. The cannula head 114 is attached to the distal side of the tubular body 102 by an overclamping nut 120 using a threaded or female coupling 122 for fast attachment. As shown in FIG. 1, the overclamping nut 120 has outer ribbed surfaces 124 adapted to be grasped for twisting (or untwisting) it into place. Tubular body 102 and cannula 112 define an elongated hollow chamber.

Figure 5:
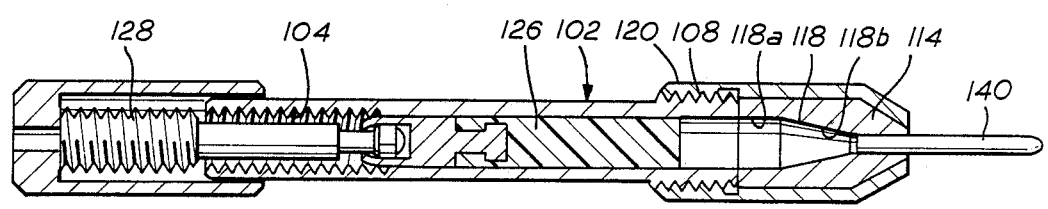
FIG. 5 is a side cross-sectional view of the tool of FIG. 1.
Figure 7:
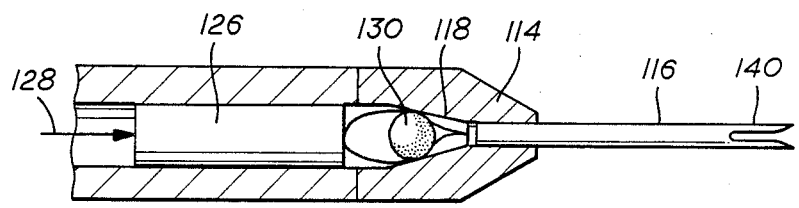
FIG. 7 is an enlarged view of the distal end of the tool of FIG. 1 illustrating in a simplified manner the elastomeric plunger thereof initially engaging the compressible intraocular lens.
Figure 8:
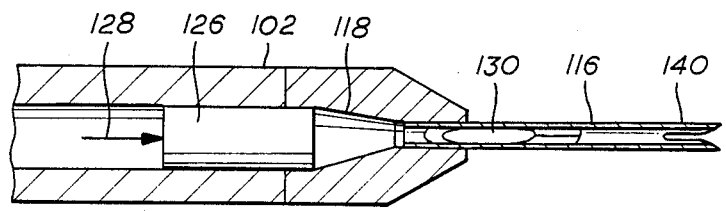
FIG. 8 is a view similar to FIG. 7 illustrating the plunger forceably extruding the lens into the cannula.

A soft elastomeric plunger 126 is inserted into the proximal end of the tubular body 102 and driven by a screw 128 or by other mechanical, hydraulic, electrical or other equivalent means into the tubular body 102. The plunger 126 is shown in FIG. 5 inserted into the tubular body 102. Referring to FIG. 7, the intraocular lens 130 is shown positioned in the inner loading chamber 118 and the plunger 126 is shown positioned to initially engage the lens 130. As the screw 128 is turned, the plunger 126 is forced towards the cannula member 116 and the lens 130 is pressed against the inside converging surfaces of the cone 118 which thereby exert a radial force against it, and the axial driving motion (shown by the arrow) of the plunger 126 pushes the radially-deformed lens 130 into its extruded position in the cannula member 116, as shown in FIG. 8.

This extrusion actually reduces the cross-sectional area of the optical zone of the lens 130 so that it can be delivered into and through a very small cannula member or system. After having been thereby extruded into the cannula member 116, the plunger 126 is removed from the tubular body 102 and a push rod 134 is inserted therein.

The push rod 134, which is shown in FIGS. 3 and 4, includes a narrow elongated rod 136 configured to fit into the narrow cannula member 116 and having a soft material at its tip 138 to protect the lens 130 against damage when impacted thereby. The push rod 134 is driven, similar to the plunger, by a screw 139 (or 128), or other mechanical, hydraulic, electrical or suitable means, towards the distal body 140 of the cannula tip 112 which is the outlet end of the cannula member and elongated hollow chamber.

Figure 6:
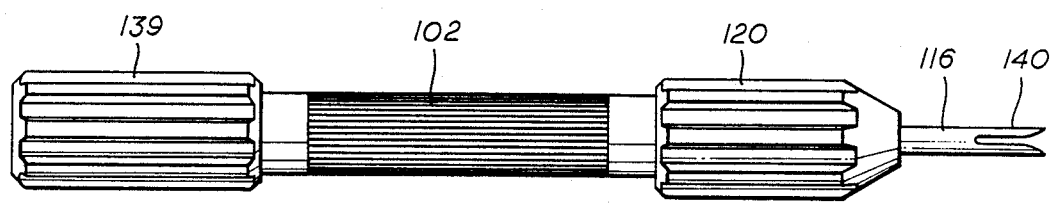
FIG. 6 is a side view of the tool of FIG. 1 illustrated in its assembled condition.

Accordingly, the operating procedure for tool 100 is very simple. A lubricated soft intraocular lens 130 is inserted with forceps (not shown) into the inner loading chamber 118 of the cannula head 114. The cannula head 114 is aligned with and firmly attached to the tubular body 102 by twisting the overclamping nut 120 into place as depicted in FIGS. 5 and 6. The elastomeric plunger 126 is inserted into the tail or proximal end of the tubular body 102 and then with a mechanical screw 128 (or other means) is driven until the lens 130 is extruded and fully loaded in the cannula member 116. Thus the lens is pressed from the back by the plunger 126 and pushed through the cone into the smaller cannula opening, and is not thereby, from a technical point of view, compressed but rather extruded into the cannula member 116. Reference to the compressing means herein, however, will be taken as including extruding means. The plunger 126 is then removed from tubular body 102 and replaced with a push rod 134 which pushes the lens out from the cannula member 116 and into the eye by twisting its screw member end 139.

There is no need initially, or at any time, to hand roll the intraocular lens. The loading procedure is quick and accurate and the intraocular lens 130 is delivered in a very controlled manner into the eye. The lens can be inserted thusly through an incision in a size range of 1.5 to 5.0 mm. depending upon the property of the material of the intraocular lens and the needed dioptric lens power.

Figure 38:
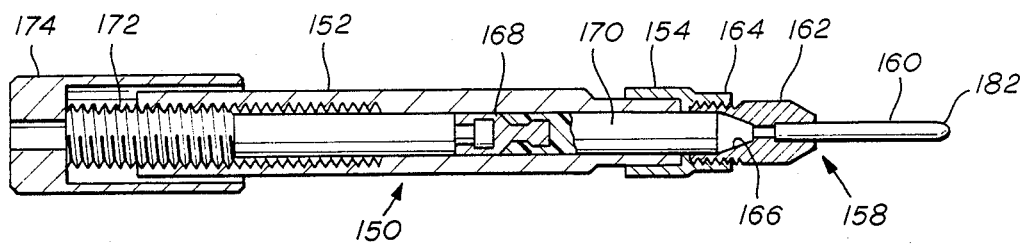
FIG. 38 is a side cross-sectional view of another embodiment of the insertion tool of the present invention.

A modified tool design of this invention is illustrated in FIG. 38 and generally at 150. Tool 150 comprises a tube body 152 having a proximal end, a distal end and a channel extending therethrough. The tube body functions as a plunger housing. A female coupling 154 is provided at the distal end by being press fit to or injection molded with tube body 152 to thereby define a single piece. The cannula shown generally at 158 has an elongated cannula member 160 and at its proximal end a cannula head 162 secured to the elongated cannula member. Cannula 158 and tube body 152 generally define an elongated hollow chamber.

Tube body 152 defines a male coupling and is threaded at a steep angle to define a Luer lock 164 with the female coupling 154. The Luer lock is similar to that used to attach a needle to a syringe. The cannula head 162 is internally configured to define a cone 166 converging and opening towards the channel of the cannula member 160.

A plunger 168 is fitted into the channel of the tube body 152. The plunger has a rubber or elastomeric boss 170 at its distal end and a screw 172 at its proximal end. The screw 172 has a gripping head 174 which when grasped and turned relative to the tube body 152 causes the boss 170 to advance towards the cone 166 and to press an intraocular lens, such as lens 130, against and through the cone and extrude it into the cannula member 160.

The cannula head 162 can be formed of a clear plastic material, and boss 170 colored a dark color such as brown, so that the intraocular lens and boss are visible through it and it can be readily determined when the lens has been extruded into the cannula member by the boss and thus when it is no longer necessary to continue turning the gripping head 174.

Figure 39:
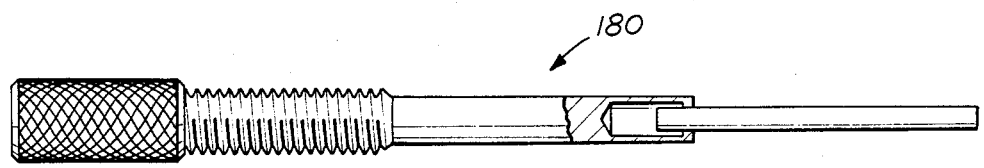
FIG. 39 is a side partially-sectional view of the push rod to be used with the tool of FIG. 38.

After the lens has been extruded into the cannula member 160, the screw 172 is removed from the tube body 152. Then similar to the embodiment of FIG. 1 a push rod 180, shown in FIG. 39, is inserted into the channel of the tube body 152 and its distal end is advanced through the cannula member 160 and against the lens extruded therein to eject the lens out of distal tip 182 of the cannula member 160, or the outlet end of the elongated hollow chamber and into the eye. Distal tip 182 is configured to allow for the gradual controlled release of the extruded lens from the cannula member into the eye. Examples of suitable tip configurations are illustrated in FIGS. 30–37 and described later in detail.

Figure 40:
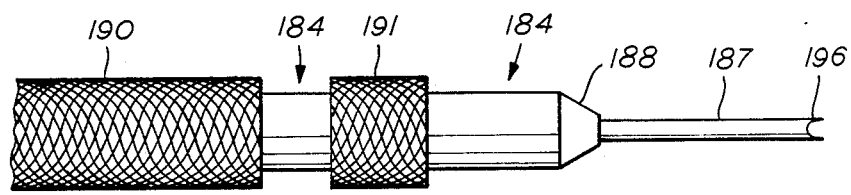
FIG. 40 is a fragmentary side view of a variant of the tool of FIG. 38.
Figure 41:
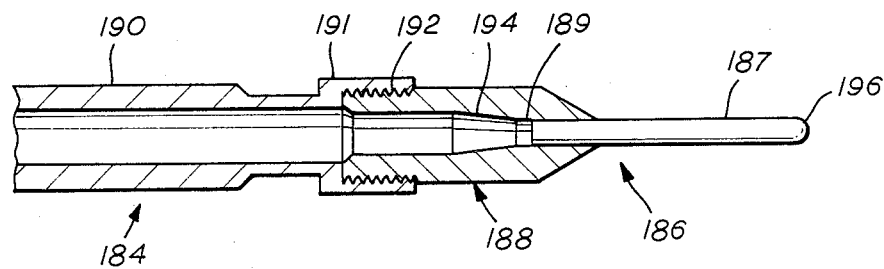
FIG. 41 is a cross-sectional top view of the tool of FIG. 40.

A variant of the tool design of FIG. 38 is shown generally at 184 in FIGS. 40 and 41. Tool 184 similarly includes a cannula 186 formed by an elongated cannula member 187 and a cannula head 188 connected thereto. The cannula member 187 has a flange 189 at its proximal end fitting into a recess in the cannula head 188 to secure the cannula member to the cannula head, as shown in FIG. 41.

The tube body 190 has a threaded sleeve 191 forming a female coupling into which the proximal male threaded coupling end 192 of the cannula head 188 is threaded in a conventional manner to attach the cannula 186 to the tube body 190. The cannula head 188 is similarly constructed of a clear plastic material allowing the cone 194 formed therein and the positioning of the lens and plunger tip therein to be easily visualized by the user.

When the plunger tip has extruded the lens into the cannula member (as can be visualized) it is removed from the tube body 190, and the push rod 180 inserted therein to eject the lens out of the distal cannula tip 196. The tip, though pictured with an alligator type of release, can be configured with any of the designs of FIGS. 30–37 or their equivalents.

Another embodiment of the present invention is illustrated in FIGS. 11 through 16, and the loading tool shown therein generally at 200 includes a head 202 with deep narrow slots 203 into which are inserted cams with protruding hand levers 204, 206. A pair of jaws 207, 208 is provided with half elliptical grooves 210, as illustrated in FIG. 14. A tubular body 212 is provided having a ring slide holder 214. The head 202 has two threads one on each side; the tail thread 216 is used to attach the tubular body 212 and the front thread or coupling 218 is used for fast attachment by the overclamping nut 220 to clamp down the cannula system, which is shown in FIG. 11 and in greater detail in FIG. 12 at 222.

The lens is squeezed between grooves 210 by the force of the cams 224 rotating about the pivot pins 226, as shown in FIG. 13, by the operation of the hand levers 204, 206. When the hand levers 204, 206 are squeezed towards the tubular body 212 the jaws 207, 208 are positioned so as to be just touching one another and the lens is squeezed in the grooves 210 and thereby formed in an elliptical shape. The cross-section of this ellipse is smaller than the cross-section of the original lens. The hand levers 204, 206 are held in this position against the tubular body 212 by positioning ring slide holder 214 over them as shown in FIG. 15. The push rod 234 operated by a screw mechanism 236, or other mechanical, hydraulic, electrical or equivalent means, then pushes the lens out of the cannula 222.

The loading procedure for tool 200 is accordingly very simple. The cannula system 222 and overclamping nut 220 are removed from the head 202. The hand levers 204, 206 are released from the ring slide holder 124 and rotated about the pivot pins 226 so that the angle between the hand levers 204, 206 and tubular body 212 is approximately sixty degrees, as shown in FIG. 11, to thereby open the jaws 207, 208.

A lubricated soft intraocular lens is inserted between the jaws 207, 208 into a space created by the half elliptical grooves 210 through the cannula system mounting hole 240 as depicted in FIG. 11. The hand levers 204, 206 are then squeezed towards the tubular body 212 and held against it by positioning ring slide holder 214. By this action the cams 224 squeeze the jaws 207, 208 and thereby squeeze the lens.

Subsequently, the cannula system 222 is inserted into its hole or opening 240 in the head 202 and firmly tightened down by overclamping nut 220. The squeezed lens is then pushed out of the tool 200 by driving the push rod 234 against it. The jaws 207, 208 automatically align the lens with the axis of the cannula system 222. The push rod 234 delivers the intraocular lens through the cannula 222 and out of the cannula tip 242 in a very controlled manner into the eye. Alternatively, a plunger-push rod arrangement as previously described for tool 100 can be provided.

Figure 26:
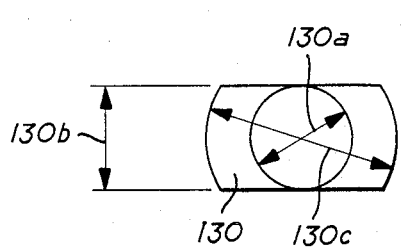
FIG. 26 is a plan view of an intraocular lens which can be inserted with the insertion tools of the present invention.

Tools 100 and 200 are designed for current market soft lenses 130. The average usable lens is a six mm optic diopter $130a$ with a six mm flange $130b$ width, and having an overall length $130c$ of 10.0 to 13.0 mm, as shown in FIG. 26. However, this does not mean that the tools cannot be used for different dimensions (smaller or larger) or different shapes. Lenses having all anticipated ranges of diopter powers can be inserted by these tools. For the most clinically demanded lenses with diopter powers ranging about eighteen to twenty-five diopters, the maximum incision required would be around 1.5 mm to 5.0 mm depending on the lens material and its refractive index.

The incision size for the present insertion tools can be used with any footplate dioptric lens made of silicone or any other similar flexible material. An example of a currently available footplate haptic lens which can be used is the Staar AA4004 intraocular lens which is a 6.0 mm by 11.5 mm foldable silicone lens designed for placement in the ciliary sulcus.

Figure 17:
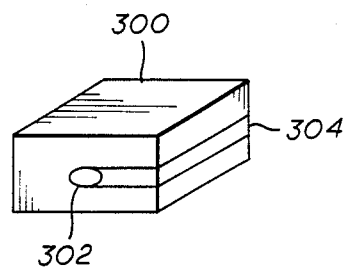
Figure 18:
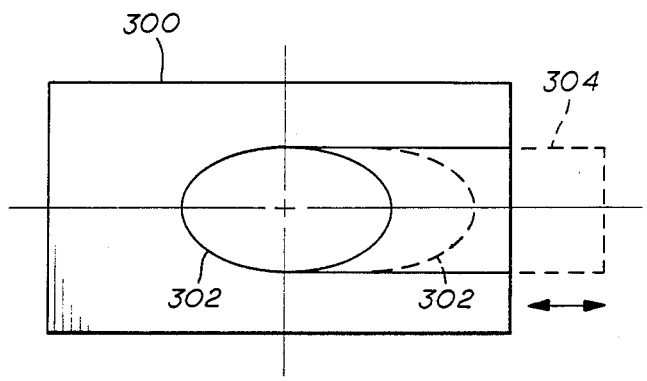
Figure 19:
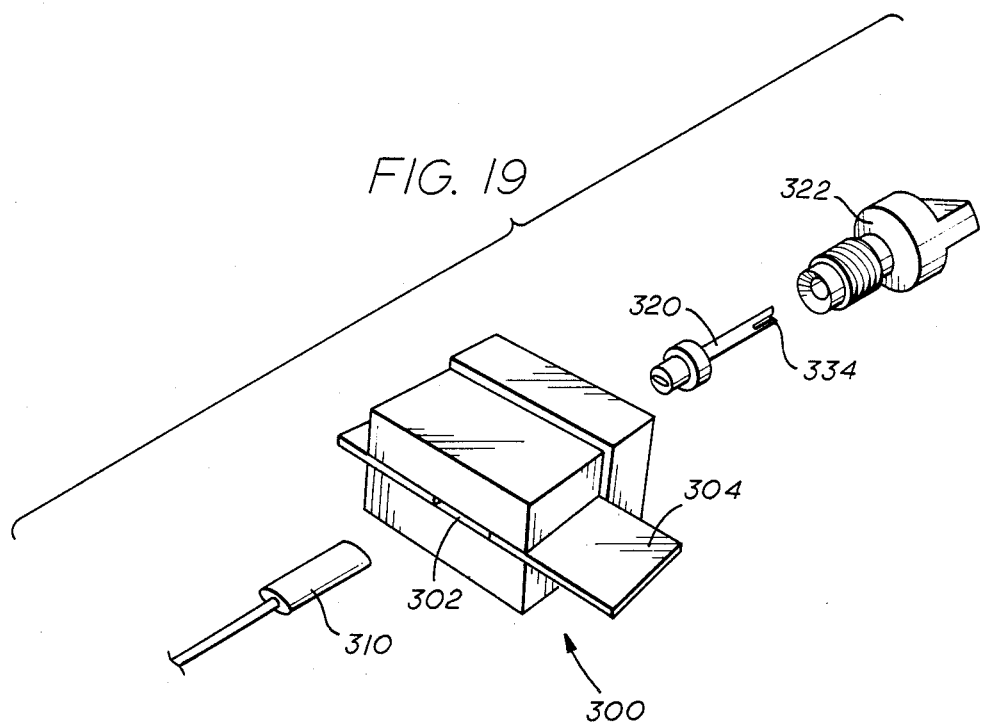

Another system for loading and inserting a compressible intraocular lens through a small incision is shown in simplified step-by-step manner in FIGS. 17 through 26. The loading block of this embodiment is shown in FIG. 17 at 300. It includes a channel 302 with a roughly elliptical shape one half of which is free to slide, as shown by the sliding plate 304 of FIG. 18 or both of sliding plates each having a half of elliptical shape are free to slide as shown on FIG. 21, such that the major axis of the channel cross section can be made larger or smaller, while the minor axis remains constant at approximately 1.5 mm.

The channel 302 is opened far enough to allow an undeformed elastomeric intraocular lens to be inserted therein. Lubricant is placed in the channel 302 and the lens 306 inserted therein as by forceps 308 as depicted in FIG. 20. The channel 302 is then closed by sliding the sliding plate 304 inward to approximately 3.0–3.5 mm thereby forming the lens 306 to the closed shape of the channel and completely enclosing it therein. The plate 304 is locked into position by plate lock 312 depicted in FIG. 21. A cannula 320 with a cross-sectional shape matching that of the closed channel is aligned with the channel 302, using alignment tool 310, and affixed to the loading block by a cap member 322.

Figure 24:
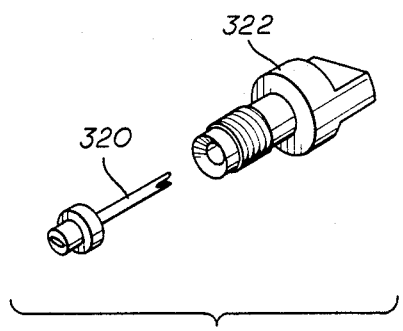

As shown in FIG. 22, a displacing guide 314 is attached to the loading block 300 and the displacing plunger 316 inserted therein. The plunger 316 is then forced by mechanical, hydraulic or other means 318 towards the cannula 320, as illustrated by the arrow in FIG. 23, and against the lens 306 forcing the squeezed lens and displacing it into the cannula 320. After the squeezed intraocular lens has been forced into the cannula 320, the cannula 320 is removed from the loading block 300 as shown in FIG. 24 and separated from cap member 322.

Figure 25:
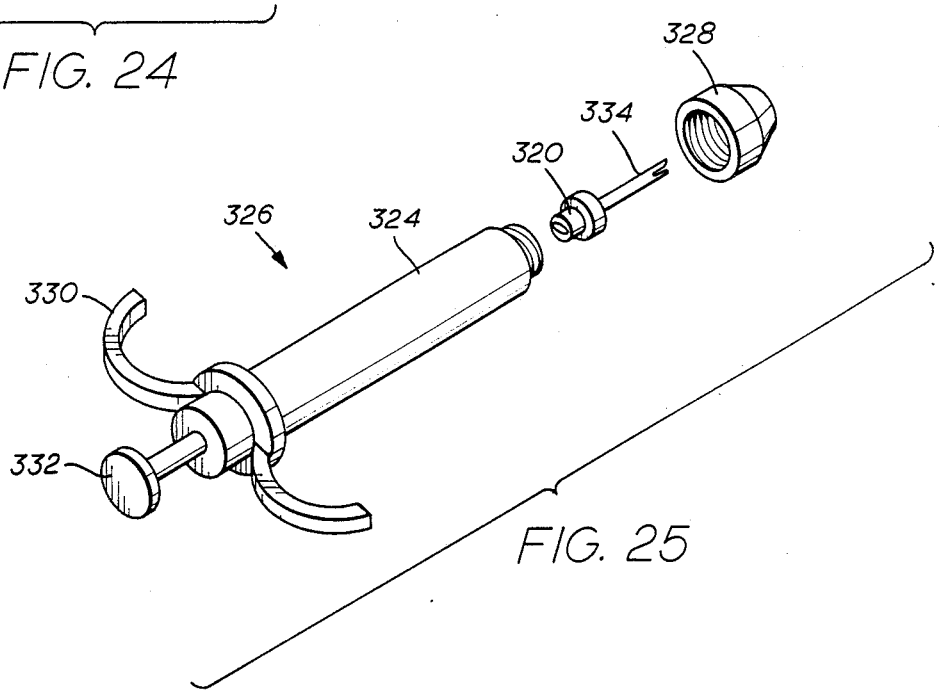
FIG. 25 illustrates the assembly of the cannula into the insertion tool step.

The cannula 320, with the intraocular lens therein, is then fitted into the handpiece 324 of insertion tool 326 illustrated generally in FIG. 25 and the overclamping nut 328 secured thereto to hold it together. The insertion tool 326 allows the cannula 320 to be inserted through the same or slightly larger incision in the eye made for the phacoemulsification cannula. As shown the insertion tool 326 has hand or finger handles 330 (or a separate power supply) and a plunger 332 adapted to be controllably operated as by the surgeon's thumb for pushing or injecting the lens out of the tip 334 of the cannula 320 and into the eye.

Figure 27:
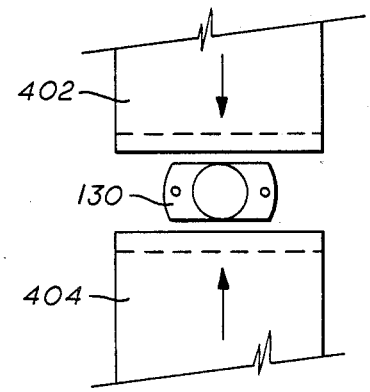
FIG. 27 is a fragmentary cross-sectional side view illustrating in a simplified manner an assembly for squeezing an intraocular lens of the present invention.

Referring to FIGS. 27 and 28, an intraocular lens 130 can be squeezed (have its cross-sectional area reduced) by moving two slides 402, 404 towards one another and towards lens 130 positioned between them. The slides can be moved in a parallel motion or rotated about pivots. Alternatively, a single slide 406 can be provided and moved towards a stationary housing member 408, as shown in FIG. 29. The channel thereby defined can have any suitable cross-sectional configuration including circular, oval, elliptical and diamond as shown in FIG. 61. Exemplary devices for effecting this squeezing system include tool 200 and loading block 300, both of which were previously described. Another forcing (extrusion) system of this invention is depicted for example by the cone 118 and elastomeric plunger 126 arrangement of FIG. 7.

The tips of the cannulas according to any of the previously (or later) described embodiments are preferably configured to allow for the gradual release of the stored elastic energy of the extruded lens as it is ejected from the cannula. A first embodiment of the cannula tip is shown in FIGS. 30 through 32 generally at 500 to include a split end. The split end, or alligator type for releasing energy is most clearly illustrated in FIG. 31, and includes two extending contoured lips 502, 504 oppositely disposed about the larger axis of the oval cannula configuration. FIG. 32 depicts the oval configuration as having a minor diameter of about 1.25 mm and a major diameter of approximately 3.0 mm. In the side view as depicted in FIG. 31 the slot 506 is shown configured as an ellipse with the upper and lower curves 507, 508 facing one another.

As can be appreciated and referring to FIGS. 10 and 16, this unique design allows for the controlled release of the stored elastic energy of the extruded lens thereby providing for the controlled insertion and placement of the lens into the eye. This prevents the lens from jumping or springing open and damaging the inside of the eye upon release therein. It also does not require that any type of cannula jaw arrangement be provided and opened within the eye which would increase the chances of endothelial or other touch.

Other configurations of the cannula tip having the above-described controlled release advantages are possible and examples thereof are illustrated in FIGS. 33-37. FIGS. 33 and 34 illustrate at 510 a second tip design— a split end, alligator type of tip. It is very similar to tip 500 with outwardly extending lips 512, 514 except that slot 516 is configured differently. It is seen in FIG. 33 that the curves 517, 518 of slot 516 face the opposite directions. In the cannula tip 520 of FIGS. 35 and 36, a side angle cut 522 is provided as best shown in the profile of FIG. 35. A slot 524 can be formed preferably at the upper or proximal point of angle cut 522. Tip 530 of FIG. 37 simply includes a plurality of spaced radial holes 532 about the circumference. As depicted, the holes can be formed in a pattern of two parallel bands 534, 536.

Figure 42:
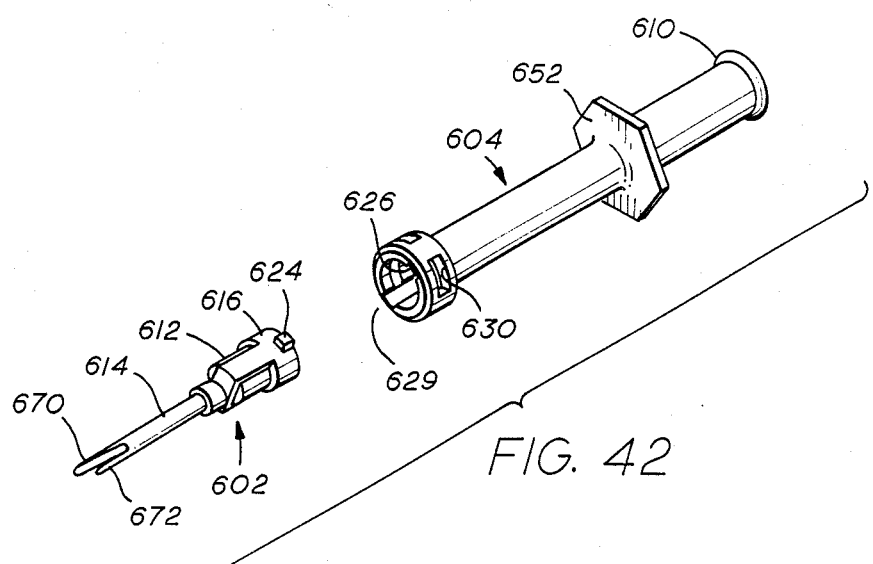
FIG. 42 is a perspective view of the cannula body and plunger housing portions of another insertion tool of the present invention whose parts are illustrated in exploded relation.
Figure 43:
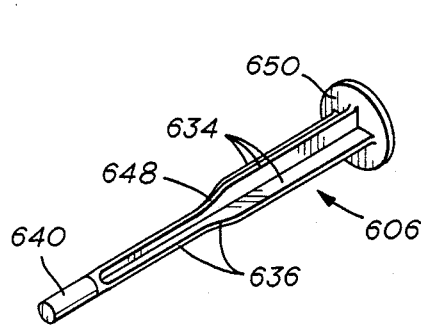
FIG. 43 is a perspective view of a plunger for the tool of FIG. 42.
Figure 44:
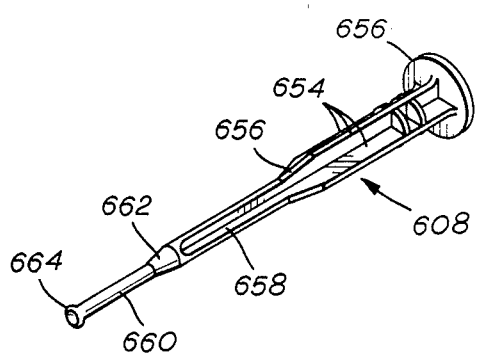
FIG. 44 is a perspective view of a push rod for the tool of FIG. 42.

Another embodiment of the invention is shown in FIGS. 42–52, which is a simplified version of the insertion tool that is formed of inexpensive plastic and disposable after a lens has been implanted in the eye. As shown in FIGS. 42 and 47, the instrument is similar in design to a syringe and includes a cannula body 602 that is connected to a tubular plunger chamber 604 through a bayonet-type locking mechanism described in greater detail below. A plunger 606 shown in FIG. 43 and a push rod 608 shown in FIG. 44 are designed to be inserted into a proximal end 610 of the plunger housing 604 in order to extrude and push a compressible intraocular lens for implantation in an eye as described in detail above in conjunction with other embodiments of the invention.

The cannula body 602 includes a loading chamber 612, a cannula member 614 and a cannula holder 616. The loading chamber 612 is preferably formed of a transparent material so the surgeon can observe the location and condition of a compressed intraocular lens in the loading chamber 612. The cannula holder 616 can also be formed of a transparent material, as can the cannula member 614 which would normally be formed of stainless steel.

The cannula member 614 is formed as a separate element with a flared proximal end 618 (see FIG. 47) that is adapted to engage the distal end 620 of a loading chamber 612 so that the inner passageways of the cannula 614 and of the loading chamber 612 are aligned. The passageway of the loading chamber 612 includes a cylindrical cross-sectional portion 612a into which a lens can be loaded (see FIGS. 48–52) and a tapered conical portion 612b for compressing and intraocular lens as described above, the cross-sectional shape of the distal end 620 of the loading chamber 612 conforming to the cross-sectional shape of the passageway in the cannula member 614 to provide for a smooth transition of the compressed intraocular lens from the loading chamber 612 to the cannula member 614.

A bayonet locking mechanism described in greater detail below includes the cannula holder 616 which has an inner configuration that engages the flared proximal end 618 of the cannula member 614 and a flared proximal end 622 of the loading chamber 612 for holding them together and locking them to the plunger housing 604. The cannula holder 616 includes a pair of bosses 624 that are adapted to engage cooperating slots 626 formed in the inner surface of a locking ring 628 on the distal end 629 of the plunger housing 604. After the bosses 624 are inserted into the slots 626, they are rotated into cooperating ring openings 630 for locking the cannula body 602 to the plunger housing 604.

The plunger housing 604 includes a smooth inner passageway 632 and 638 adapted to receive the plunger 606 and push rod 608 shown in FIGS. 43 and 44, respectively. As described in greater detail above, the plunger 606 is used to push and force an intraocular lens into a passageway in the cannula member 614 after the lens has been inserted in the proximal end 622 of the loading chamber 612 (as described in greater detail below) and the cannula body 602 is locked onto the plunger housing 604. The plunger 606 is formed with a plurality of longitudinal ribs 634 to provide the required strength necessary to compress an intraocular lens as described and to guide the plunger 606 along the inner passageway 632 and 638.

Figure 45:
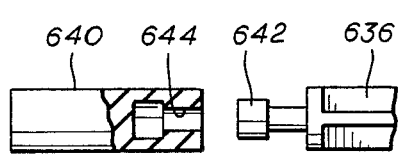
FIG. 45 is a partial sectional view of the disassembled head for the plunger of FIG. 43.

The outer surfaces of the ribs 634 are formed with a narrower neck portion 636 with a diameter slightly smaller than a narrowed portion 638 of the passageway 632. A head 640 formed of a soft material, such as a silicone elastomer, is connected to the neck portion of push rod 606 by means of an irregularly shaped projection 642 that is inserted into an opening 644 shaped to receive the projection 642 in the head 640. The head 640 deforms to allow the projection 642 to be inserted in place as shown in FIG. 45. The head 640 is preferably formed of a dark color so that it can easily be observed as it moves through the cannula body 602 so that the location and condition of an intraocular lens being forced through the cannula body 602 can easily be observed by the operating physician.

The plunger 606 also includes a tapered portion 648 which is designed to engage a similarly shaped tapered portion 650 of the plunger housing passageway 632. The pushing action is achieved by the surgeon resting the palm of his hand or thumb (not shown) on a flat outer end 650 of the plunger 606 while his or her fingers engage a hexagonal-shaped ring section 652 formed on the outer surface of the plunger housing 604.

As described above in conjunction with the other embodiments to the invention, after the intraocular lens has been compressed and is fully inserted into the passageway of the cannula member 614, the plunger 606 is removed from the plunger housing 604 and replaced with the push rod 608 shown in FIG. 44. Similar to the plunger 606, the push rod 608 is formed with reinforcing ribs 654 that are dimensioned to fit within the inner passageway 632 of the plunger housing 604, including a flared portion 656 that engages a cooperating portion 650 of the plunger housing passageway.

The push rod 608 also includes a flattened outer end 656 to be engaged by the thumb or palm of the operator and a neck portion 658 adapted to move within the plunger housing passageway portion 638. The push rod 608 further includes an elongated rod section 660 shaped slightly smaller than the inner passageway of the cannula 614, with a conically-shaped portion 662 connecting the rod section 660 and the neck 658.

Figure 46:
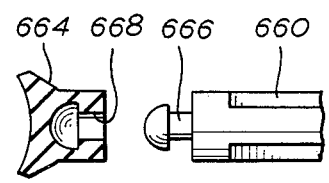
FIG. 46 is a partial sectional view of the disassembled head for the push rod of FIG. 44.

A head 664 formed of a soft material such as a silicone elastomer that is of a dark color is detachably connected at the distal end of the rod section 660 through a projection 666 and shaped opening 668 arrangement shown in FIG. 46 that is similar to the one described in conjunction with FIG. 45 for the plunger 606. The head 664 is cup-shaped on its distal end for engaging the compressed intraocular lens and pushing it through the passageway of the cannula 614 as described above.

The distal end of the cannula member 614 is formed with a pair of lip sections 670, 672 for allowing the intraocular lens to gradually be pushed from the cannula member 614 without springing open and causing possible damage to an inner portion of the eye. It will be noticed that the lip 670 is longer than the lip 672, which enables the surgeon to insert the cannula through an incision in an eye more easily than with other shapes. The surgeon can also manipulate the tool so that the shorter lip is on the posterior side of an eye during an operation, which is believed will reduce the possibility of damaging the posterior wall of the capsular bag as the lens is being inserted in place.

FIGS. 48-52 are provided to illustrate an easy method of inserting an intraocular lens 674 into the proximal end 622 of the loading chamber 612 that has been charged with an appropriate lubricant, through the use of forceps 676. FIG. 48 shows aligning the lens 674 so that the main axial plane of the lens is parallel with the axial plane of the slot formed between the lips 670, 672. As shown in FIG. 49, the intraocular lens 674 is tilted upwards so that one side of the optic portion 677 is moved against the proximal end 622 of the loading chamber 612 as shown by the arrow A, until the lens engages the loading chamber 612 as shown in FIG. 50. It will also be noticed that the more flexible haptic portion 678 of the intraocular lens 674 extends beyond the passageway of the loading chamber 612. However, with the combination of pushing the intraocular lens in the direction of the arrow A and rotating the forceps in the direction of the arrow B as shown in FIG. 50, the haptic 678 can be forced into the loading chamber 612 to a position shown in FIG. 51. As shown in FIG. 52, the lens is slightly larger than the transverse dimensions of the passageway section 612a and is positioned in a slightly bowed condition.

After the intraocular lens has been inserted as just described, the cannula body 602 is locked to the plunger housing 604 through the bayonet-type locking system described in detail above. Afterwards, the plunger 606 and push rod 608 are used to extrude and push the intraocular lens through the cannula body 602 into a position to where it can be inserted in the appropriate location in the eye. The cannula member 614 is then inserted into the eye and maneuvered to the point where the IOL can be implanted by pushing it out of the distal end of the cannula member 614.

Figure 53:
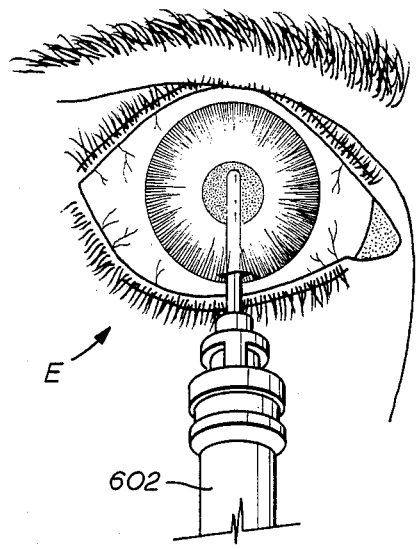
FIGS. 53–54 illustrate insertion of the tool in a human eye and positioning of an intraocular lens after it has been deposited by the instrument.
Figure 54:
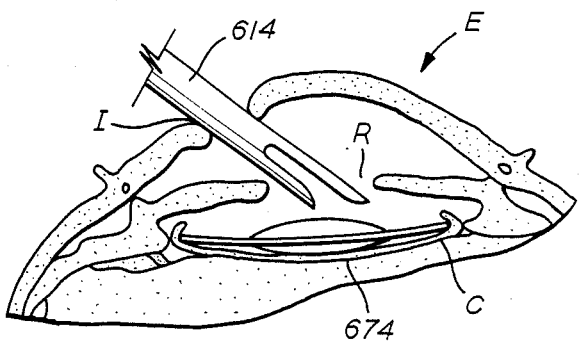
Figure 55:
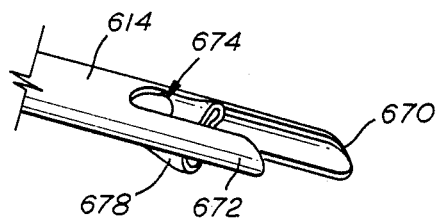
FIGS. 55–60 illustrate an intraocular lens emerging from the distal end of the insertion tool.
Figure 56:
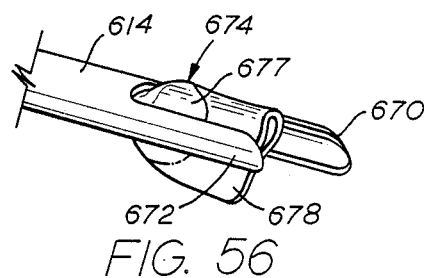
Figure 57:
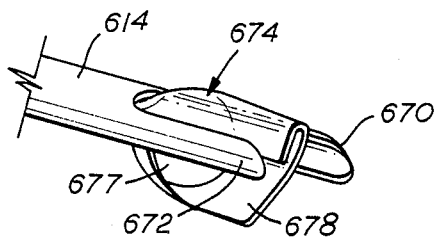
Figure 58:
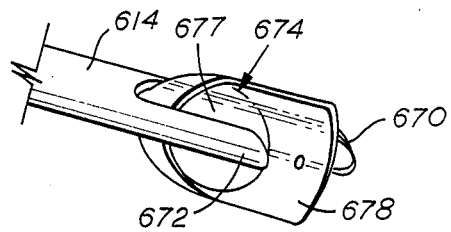
Figure 59:
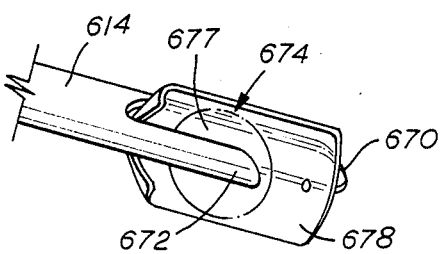
Figure 60:
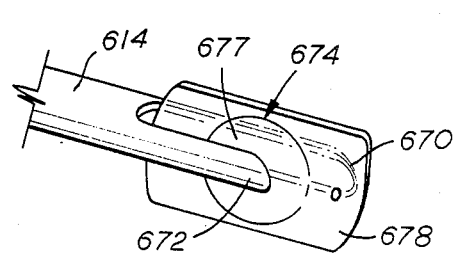

FIGS. 53 and 54 illustrate the cannula 614 of the insertion tool of the present invention inserted through an incision I formed in the cornea of a human eye E so that an intraocular lens 674 can be implanted in the eye E. As shown in particular in FIG. 54, the cannula 614 has been inserted through the incision I and through the opening IR in the iris to a position where the intraocular lens 674 can be deposited in the capsular bag C where it is implanted to replace the natural lens of the eye that has already been removed. The deposition process is illustrated in FIGS. 55-60 where an intraocular lens 674 is shown emerging from the distal end of the cannula 614 in the space between the lips 670 and 672. As the instrument is operated as discussed in detail above, the lens is pushed through the cannula 614 from the position shown in FIG. 53 where the haptic portion 678 is barely shown to where the lens totally emerges as shown in FIG. 60. This deposition process occurs while the cannula 614 is in the position shown in FIG. 54 so that when the intraocular lens 674 totally emerges from the cannula 614, it can be deposited in the position shown in FIG. 54. This way, a physician can easily implant an intraocular lens through an incision in the cornea that is no greater than the diameter of the cannula 614 multiplied by 1.6, which accommodates the round shape of the cannula 614, and provides the advantages and features discussed above.

From the foregoing detailed description, it will be evident that there are numerous changes, adaptations and modifications of the present invention which will come within the knowledge of those skilled in the art, including the exchange of different tool component configurations of the various tools described such as their tip configurations. However, it is intended that all such variations not departing from the spirit of this invention be considered as within the scope thereof as defined by the claims appended below.

We claim:

1. A tool for preparing for insertion into an eye an intraocular lens, formed of a compressible material, comprising:
    (a) an elongated hollow chamber comprising a hollow, walled compressing chamber with a loading inlet and an outlet, at least a portion of the compressing chamber decreasing in cross-sectional area in the direction of the outlet;
    (b) first plunger means for pushing a compressible intraocular lens introduced into the loading inlet through the compressing chamber toward the outlet end, the plunger means including resilient pushing means for cooperating with the walls of the compressing chamber to compress the lens to a smaller size as the lens is pushed toward the outlet end;
    (c) cannula means connected to the outlet of the compressing chamber with an inlet for receiving the compressed intraocular lens from the outlet of the compressing chamber; and
    (d) second plunger means for pushing the compressed intraocular lens through the cannula means and into an eye.

2. The tool of claim 1, wherein the cannula means includes a passageway that is uniform in cross-section along its length.

3. The tool of claim 2, wherein the cannula means includes a passageway that is circular in cross-section.

4. The tool of claim 2, wherein the cannula means includes a passageway that is elliptical in cross-section.

5. The tool of claim 2, wherein the cannula means includes a passageway that is oval in cross-section.

6. The tool of claim 2, wherein the cannula means includes a passageway that is a parallelogram in cross-section.

7. The tool of claim 1, wherein the cannula means includes a outlet end that comprises a gradual release means for allowing the compressed lens to gradually release its stored energy and gradually return to its initial shape as the lens is pushed out of the outlet end of the cannula.

8. The tool of claim 7, wherein the gradual release means includes configuring the outlet end to include a pair of contoured lips on opposite sides of the outlet end separated by a generally v-shaped notch.

9. The tool of claim 8, wherein the lips are about the same length.

10. The tool of claim 8, wherein one of the lips is longer than the other lip.

11. The tool of claim 8, wherein the outlet end includes a plurality of spaced radial openings communicating with the passageway.

12. The tool of claim 11, wherein the radial openings are arranged in at least two parallel bands.

13. The tool of claim 7, wherein the gradual release means includes configuring the outlet end so that one side of the outlet end is longer than the other side.

14. The tool of claim 13, wherein the side opposite the longer side includes a slot extending away from the end.

15. The tool of claim 1, wherein at least a portion of the elongated chamber is formed of a transparent material.

16. The tool of claim 1, wherein the elongated chamber and the cannula means are formed of separate components and further including connecting means for connecting the elongated chamber and cannula means so that the outlet of the elongated chamber and inlet of the cannula means are aligned.

17. The tool of claim 16, wherein the compressing means includes a housing with an elongated channel having at least one longitudinal wall communicating with the outlet, sliding compressing means for cooperating with the channel and compressing an intraocular lens against the longitudinal wall, clamping means for clamping the sliding compressing means in place after the intraocular lens is compressed.

18. The tool of claim 17, wherein the longitudinal wall and the compressing means are shaped to form an elliptical channel when the sliding compressing means is moved toward the longitudinal wall.

19. The tool of claim 16, wherein the compressing means includes a housing with a longitudinal slot communicating with the outlet, a pair of sliding compressing means moveable toward each other in the slot for compressing an intraocular lens between them, clamping means for clamping the sliding compressing means in place after the intraocular lens is compressed.

20. The tool of claim 19, wherein the portions of the pair of sliding compressing means facing each other are shaped so that the longitudinal slot is elliptical in cross-section.

21. The tool of claim 19, wherein the portions of the pair of sliding compressing means facing each other are shaped so that the longitudinal slot is round in cross-section.

22. The tool of claim 19, wherein the portions of the pair of sliding compressing means facing each other are shaped so that the longitudinal slot is oval in cross-section.

23. The tool of claim 19, wherein the portions of the pair of sliding compressing means facing each other are shaped so that the longitudinal slot is diamond-shaped cross-section.

24. The tool of claim 16, wherein the compressing means includes a housing with an elongated channel communicating with the outlet, a pair of cams mounted on the housing to move back and forth into the channel, a pair of hand levers connected to the cams for moving the cams toward and away from each other for compressing an intraocular lens in the channel when the cams are moved toward each other.

25. The tool of claim 1 wherein the elongated chamber further comprises a plunger housing, that communicates with the inlet of the compressing chamber, means for connecting the plunger housing with the compressing chamber, wherein the first and second plunger means are movable back and forth in the plunger housing.

26. The tool of claim 25, wherein the plunger includes first and second plunger sections, the plunger housing and first plunger section having cooperating threads so that rotation of the first plunger section relative to the housing will cause the second plunger section to move longitudinally relative to the housing.

27. The tool of claim 25, wherein the plunger housing has finger hold means on its outer surface, and the plunger includes an outer end engageable by an operator so that the plunger housing can be held with one hand for moving the plunger longitudinally in the plunger housing.

28. The tool of claim 1, wherein the compressing chamber is tapered along at least a portion of its length.

29. The tool of claim 28, wherein the compressing chamber includes a first portion of uniform cross-section adjacent to the inlet opening, and a second portion of gradually decreasing cross-section extending between the first portion and the outlet opening.

30. The tool of claim 28, and further including a plunger housing, and connecting means for removably connecting the comprising chamber to the plunger housing, the plunger housing being aligned with the compressing chamber.

31. The tool of claim 30, wherein the loading chamber is formed of a transparent material.

32. The tool of claim 30, wherein the connecting means includes cooperating threads formed on the compressing chamber and plunger housing.

33. The tool of claim 30, wherein the connecting means includes a bayonet locking system including a flange formed at the inlet opening of the cannula means, a sleeve member with at least one boss adapted to fit over the cannula means and engage the flange, a receiver with a slot and opening for each boss formed in the plunger housing for receiving the bosses and locking the cannula means to the plunger housing.

34. The tool of claim 30, wherein the plunger housing and the first and second plungers include cooperating threads so that the first and second plungers move longitudinally in and out as their threads are rotated relative to the housing.

35. The tool of claim 1, wherein the resilient pushing means includes a head adapted to compress a compressible intraocular lens by pushing it through the compressing chamber and into the cannula means.

36. The tool of claim 35, wherein the second plunger means includes a neck portion adapted to fit in the cannula means and a head connected to the neck portion adapted to push the compressed intraocular lens through the cannula means.

37. The tool of claims 35 or 36, wherein the head is formed of a relatively soft deformable material for preventing damage to the intraocular lens.

38. The tool of claim 37, wherein the head is cup-shaped on the portion adapted to engage the intraocular lens.

39. The tool of claims 35 or 36, and further including releasable connection means between the head and plunger.

40. The tool of claims 35 or 36, wherein the plunger housing and first and second plunger means include cooperating surfaces so that the respective plunger means can move longitudinally relative to the housing.

41. A method of preparing an intraocular lens formed of a compressible material for insertion into an eye, comprising the steps of:
(a) providing a loading chamber, a cannula having a proximal end communicating with said loading chamber and an opposite distal end, an extruding means for extruding a compressible intraocular lens from said loading chamber into said cannula including a first resilient pushing means for cooperating with the walls of the loading chamber to compress the lens to a smaller size as the lens is extruded, and an ejecting means for ejecting the extruded lens out said distal end including a second resilient pushing means,
(b) positioning a compressible intraocular lens into said loading chamber,
(c) extruding with said extruding means said lens from said loading chamber into said cannula through said proximal end.

42. The method of claim 41 and further comprising the step of lubricating said loading chamber before step (b).

43. The method of claim 42, and further including the step of connecting the loading chamber and extruding means after step (b).

44. The method of claim 41 wherein step (b) further includes moving a lens with an optic and flexible flanges projecting from the optic at an angle to the longitudinal axis of the said loading chamber into engagement with the entrance of said loading chamber, and pushing said lens forward into said chamber while rotating said lens until it is parallel to said axis, and pressing said lens forward and into the loading chamber.

45. The method of claim 41, wherein step (c) includes using a plunger as the resilient pushing means to push the lens from the chamber into the cannula.

46. The method of claim 41, wherein step (c) includes pushing the lens through a chamber that is at least partially tapered toward the cannula.

47. The method of claim 46, wherein step (c) includes using a plunger with an end formed of a deformable material for pushing the lens through the chamber and replacing the plunger with a push rod with an end formed of a deformable material for pushing the lens through the cannula.

48. The method of claim 41, wherein step (a) includes providing the distal end with means for allowing the lens to gradually release its stored energy as the lens emerges from the cannula.

* * * * *